(12) United States Patent
Yamauchi et al.

(10) Patent No.: US 7,066,011 B2
(45) Date of Patent: Jun. 27, 2006

(54) LIQUID CHROMATOGRAPH AND ANALYSIS SYSTEM

(75) Inventors: Yoshi Yamauchi, Hino (JP); Tohru Natsume, Tokyo (JP); Toshiaki Isobe, Hachioji (JP)

(73) Assignee: Nano Solution, Inc., Tokyo (JP)

( * ) Notice: Subject to any disclaimer, the term of this patent is extended or adjusted under 35 U.S.C. 154(b) by 0 days.

(21) Appl. No.: 10/479,412

(22) PCT Filed: Apr. 8, 2001

(86) PCT No.: PCT/JP02/03476

§ 371 (c)(1),
(2), (4) Date: Jul. 19, 2004

(87) PCT Pub. No.: WO02/101381

PCT Pub. Date: Dec. 19, 2002

(65) Prior Publication Data

US 2005/0016263 A1    Jan. 27, 2005

(30) Foreign Application Priority Data

Jun. 7, 2001    (JP) .............................. 2001-171917

(51) Int. Cl.
  *G01N 1/00*    (2006.01)
  *G01N 30/00*   (2006.01)
  *B01D 15/08*   (2006.01)
(52) U.S. Cl. .................. 73/61.59; 73/61.56; 210/198.2
(58) Field of Classification Search ............... 73/64.56, 73/61.59; 210/198.2, 656
See application file for complete search history.

(56) References Cited

U.S. PATENT DOCUMENTS 3,373,872 A * 3/1968 Hrdina .................... 210/198.2

3,536,450 A    10/1970 Dus et al.
(Continued)

FOREIGN PATENT DOCUMENTS

WO    WO 00/08460    2/2000
(Continued)

OTHER PUBLICATIONS

International Search Report for Application No. PCT/JP02/03476 dated May 21, 2002.
(Continued)

*Primary Examiner*—Hezron Williams
*Assistant Examiner*—John Fitzgerald
(74) *Attorney, Agent, or Firm*—Thomas W. Cole; Nixon Peabody LLP

(57) ABSTRACT

The present invention aims to provide a liquid chromatograph, an analysis system, and a gradient elution method, which are designed to permit a gradient change of eluent with higher precision and also permit a high sensitive detection or analysis. For attaining the object, there are provided: a liquid chromatograph having at least a liquid-feeding means for flowing an eluent E at a predetermined flow rate, a sample-pouring means for pouring a sample Sm into the eluent E, and a separation-column means for separating a solute So contained in the sample Sm into components, comprising an eluent-selecting means for forming branched flow paths having predetermined volumes by dividing a flow path of the eluent E fed from the liquid-feeding means, temporally storing eluents $E_1$, $E_2$, and soon in the branched flow paths, and pouring the sample Sm into the selected eluents $E_1$, $E_2$, and so on, and means for carrying out a gradient elution of a solute So; an analysis system comprising a mass spectrometer connected to the liquid chromatograph, and a gradient-elution method using the liquid chromatograph.

9 Claims, 6 Drawing Sheets

U.S. PATENT DOCUMENTS

| | | | |
|---|---|---|---|
| 4,158,630 A | | 6/1979 | Stearns |
| 4,816,226 A | * | 3/1989 | Jordan et al. .................. 422/81 |
| 4,926,702 A | * | 5/1990 | Stephens et al. ......... 73/864.83 |
| 5,049,509 A | * | 9/1991 | Szakasits et al. ........... 436/140 |
| 5,071,547 A | * | 12/1991 | Cazer et al. ............. 210/198.2 |
| 5,108,928 A | * | 4/1992 | Menard et al. ............... 436/43 |
| 5,783,450 A | * | 7/1998 | Yoshida et al. ............. 436/161 |
| 5,952,557 A | * | 9/1999 | Ikeda et al. ................ 73/23.42 |
| 6,054,047 A | * | 4/2000 | Hindsgaul et al. ....... 210/198.2 |
| 6,063,283 A | * | 5/2000 | Shirota et al. .............. 210/656 |
| 6,080,318 A | * | 6/2000 | Gumm et al. ............... 210/659 |
| 6,149,882 A | * | 11/2000 | Guan et al. ................. 422/211 |
| 6,196,050 B1 | * | 3/2001 | Ikeda et al. .................. 73/23.2 |
| 6,210,571 B1 | * | 4/2001 | Zambias et al. ......... 210/198.2 |
| 6,426,006 B1 | * | 7/2002 | Zambias et al. ............ 210/659 |
| 6,491,816 B1 | * | 12/2002 | Petro ....................... 210/198.2 |
| 6,581,442 B1 | * | 6/2003 | Murata et al. ............. 73/61.56 |
| 2002/0020670 A1 | * | 2/2002 | Petro .......................... 210/656 |

FOREIGN PATENT DOCUMENTS

| | | |
|---|---|---|
| WO | WO-2000-72001 A1 | 11/2000 |
| WO | WO 02/101381 | 12/2002 |

OTHER PUBLICATIONS

M.T. Davis et al, "*Low Flow High-Performance Liquid Chromatography Solvent Delivery System Designed for Tandem Capillary Liquid Chromatography—Mass Spectrometry,*" *Journal of the American Society for Mass Spectrometry*, vol. 6., No. 7, pp. 572-577, Jul. 1, 1995.

European Search Report for Application No. EP-02-71-4523 dated Jun. 16, 2004.

Yukio Hirata et al., "Single Pump On-Line Mixing System for Capillary Supercritical Fluid Chromatography", *Journal of High Resolution Chromatography*, vol. 16, No. 10, pp. 601-604, Oct., 1993.

* cited by examiner

LIQUID CHROMATOGRAPH AND ANALYSIS SYSTEM

TECHNICAL FIELD

The present invention relates to a liquid chromatograph suitable for analysis on gradient elution, an analysis system having such a liquid chromatograph, and a method of gradient elution using the liquid chromatograph.

BACKGROUND ART

There is an analysis technique that utilizes the so-called gradient elution method (a gradient elution technique) in which the composition (the constituent ratio) of an elute is sequentially changed and then flowed into a separation column using a high-performance liquid chromatograph (hereinafter, referred to as "HPLC") to change the elution strength of a solute kept in the separation column.

This analysis technique has been widely applied because of its advantages in that a separation requiring a great elution time can be completed within a short time, a separation between molecules having similar structures can be allowed, and so on.

In this analysis technique, currently, it is general to feed the eluent at a flow velocity of about 1 ml/min. However, against the background of technical trends for increasing a sample-detecting accuracy by lowering the flow rate of a eluent in recent years, a HPLC being devised to feed the eluent at a flow velocity of as low as about 5 μl/min has been proposed.

However, the HPLC designed for low flow rate had a very complicated device structure, so that there was a basic technical problem in that the operation of the HPLC was difficult.

Furthermore, when a gradient elution is carried out under the conditions in which the flow velocity of the eluent is lower than 5 μl/min, it is possible to adapt a technology by which a flow path through which the eluent is transferred is split into a main stream and a subsidiary stream having a smaller inner diameter. Then, an analysis column is connected on the subsidiary stream side, and then a gradient elution analysis is performed using an eluent flowing through the subsidiary stream at a low flow velocity. However, this technology had technical problems in that a gradient elution can be hardly performed at high precision because the subsidiary stream tended to be clogged, the desired low flow rate condition of the predetermined (Sub-Ul/min) was hardly kept in stable, and it became difficult to confirm whether the flowing was occurred at a predetermined flow rate.

Therefore, the present invention intends to provide a liquid chromatograph, an analysis system, and a method for gradient elution, which are designed so as to be allowed to make a change in gradient of an eluent at higher precision and to detect or analyze at high sensitivity by subsequently feeding the eluent under stable conditions of low flow velocity.

DISCLOSURE OF THE INVENTION

For solving the above technical problems, the present invention adopts the following means.

First, there is provided a liquid chromatograph, which introduces a sample into a separation column with eluents having different compositions sequentially fed through a flow path and performs a gradient elution of a solute in the sample depending on elution strengths of the eluents, comprising: an eluent-storing means for temporally storing the eluents having different compositions in branched flow paths having predetermined volumes, where the branched flow paths are formed by dividing the flow path of the eluents; an eluent-selecting means for sequentially selecting the eluents temporarily stored in the branched flow paths and feeding the eluents toward the separation column.

More particularly, there is provided a liquid chromatograph, comprising at least (1) a high-pressure liquid-feeding means for feeding an elute at a constant flow rate, (2) an eluent-storing means for dividing a flow path of the eluent fed by the high-pressure liquid-feeding means and storing predetermined amounts of eluents having different compositions with respect to organic solvent ratio, Ph, salt concentration, or the like in the respective branched flow paths, (3) an elute-selecting means for sequentially selecting the eluents temporarily sorted in the branched flow paths and feeding the selected one toward a separation column, (4) a sample-pouring means for pouring the sample into the eluents which are sequentially fed, and (5) a means for carrying out a gradient elution of a solute contained in the sample using the separation column on the basis of elution strength of the eluent.

This liquid chromatograph has a basic characteristic of sequentially feeding the eluent at a constant flow rate without fail in a stable manner under the conditions in which the flow rate thereof is extremely low in the order of 500 nL/min or less. Therefore, it becomes possible to carry out a gradient elution of the solute components in the sample with high precision. In addition, it is designed to feed the eluent at a low flow rate, so that the solute in the elute can be condensed without fail.

In addition, an eluent-storing means is provided for temporally storing predetermined amounts of eluents having different compositions at a position in a flow path upstream from a sample-pouring means, so that there can be provided a gradient elution method in which an eluent having a desired composition can be easily fed in a stepwise or continuous manner with desired timing as needed.

Next, the liquid chromatograph of the present invention is designed to have a means for filling each branched flow path downstream from a liquid-feeding means by a syringe with a switching movement of a valve, so that the replacement or supplement of the eluent can be easily performed. Here, the eluents having different compositions may fill the respective branched flow paths under automatic control. Adopting such a means allows an increase in precision of filling the eluent.

Furthermore, at the time of initiating the analysis, it may adopt a means for sequentially feeding eluents having different compositions from the branched flow paths and storing them in the flow path extending from the discharge orifices of the respective branched flow paths to the separation column means. Such a means allows a gradient elution to be completed within a short time from the initiation of the analysis, so that the time required for the analysis can be shortened.

Furthermore, the present invention provides an analysis system in which a mass spectrometer (MASS) is connected to the separation column means of the liquid chromatography. In other words, there is provided a liquid chromatography/mass spectrometry (LC/MS).

This means permits a free selection of either of a stepwise elution method in which the composition of an eluent is changed stepwisely or a gradient elution method in which the composition of an eluent is changed continuously. Therefore, it becomes possible to effectively separate and detect within a short time at a low flow rate even in the case of a multiple-component sample that has been difficult to elute by an eluent having a single composition.

The analysis system of the present invention comprises a liquid chromatograph constructed such that the gradient elution of a solute can be performed by feeding a small flow volume of the eluent at a low flow rate, so that the detection of a solute component can be performed at high sensitivity, while extending elapsed time for the detection.

As a result, a mass spectrometry with high sensitivity can be performed because of allowing an increase in concentration of the peak of the sample separation data obtained by the mass spectrometer.

DESCRIPTION OF THE PRESENT INVENTION

Preferred embodiments of the present invention will be described with reference to the accompanying drawings.

Figure 1:
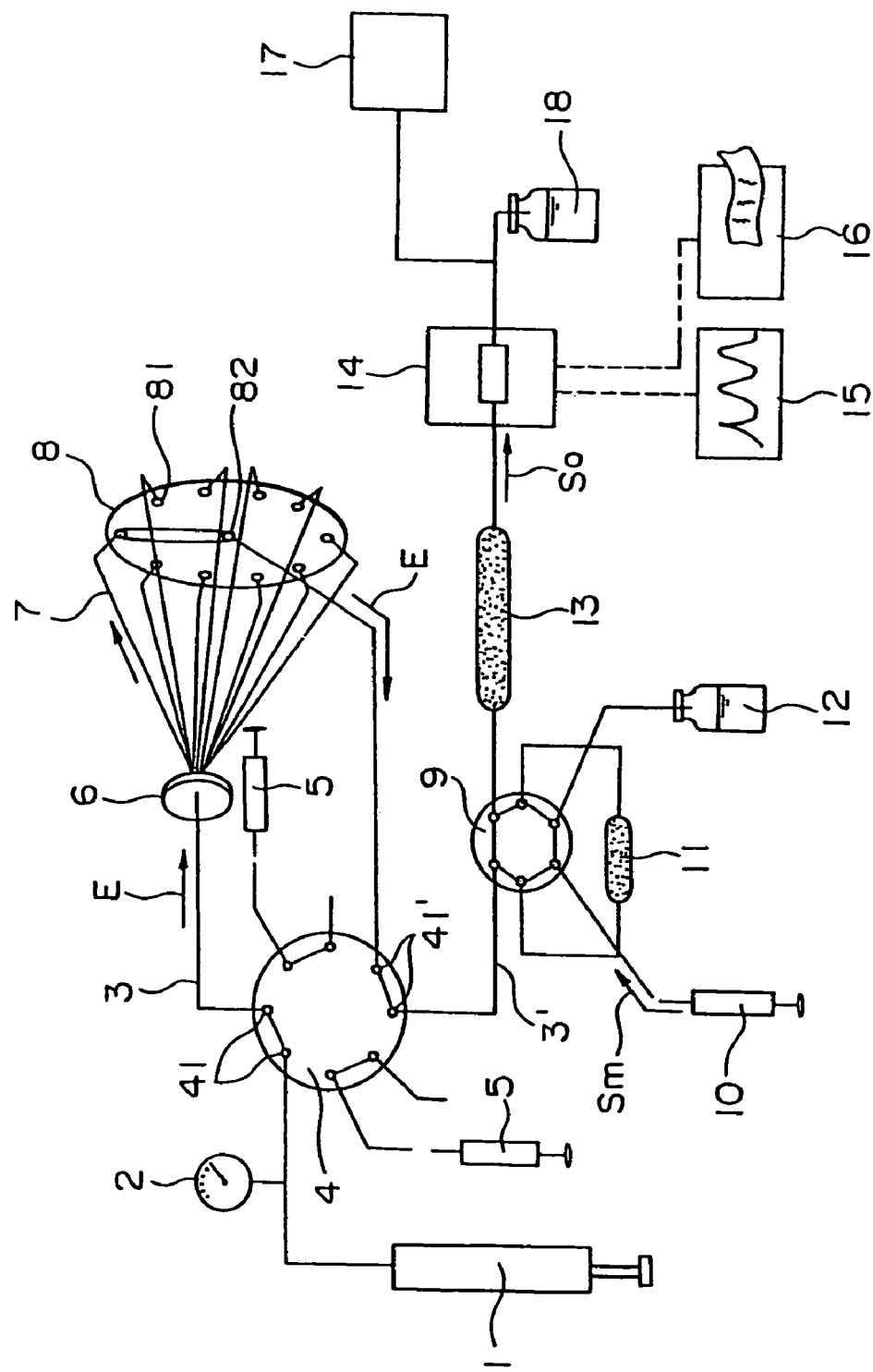
FIG. 1 is a block diagram that simply illustrates the configuration of a liquid chromatograph and the configuration of an analysis system provided with such a liquid chromatograph in accordance with the present invention.

First, FIG. 1 is a block diagram that simply illustrates the configurations of a liquid chromatograph and analysis system provided with such a liquid chromatograph, respectively, in accordance with the present invention. Hereinafter, we will describe the basic configurations of the liquid chromatograph and the analysis system of the invention, respectively.

First, the liquid chromatograph of the invention is provided with a high-pressure liquid-feeding pump 1 which is capable of feeding an eluent denoted by the symbol E in FIG. 1 in a stable manner at a low flow rate on the order of nanolitter per minute (nl/min). As such a high-pressure liquid-feeding pump 1, a plunger type pump, a microsyringe type pump, or the like is employable. Among them, however, it is preferable to adopt the microsyringe type liquid-feeding pump (infusion pump) which is more suitable to the stable feeding of a liquid at a low flow rate.

For example, as a liquid-feeding pump 1, the liquid-feeding pump PHD 2000 (manufactured by HARVARD APPARATUS Co., Ltd., U.S.A.) provided with a 250-µl-volume microsyringe manufactured by Hamilton Co., Ltd., U.S.A. can be adopted. Furthermore, as a means for feeding an eluent of the liquid chromatograph of the present invention, it is also possible to adopt a means for absorbing from the backward of a separation column 13 under negative pressure, except when a mass spectrometer is connected behind the separation column 13.

The reference numeral 2 shown in FIG. 1 is a pressure gauge for monitoring and measuring the pressure of the eluent E.

Next, a flow path 3, through which the eluent E pressure-fed from the high-pressure liquid-feeding pump 1 passes, can be formed with a stainless steel tube having an inside diameter of 0.25 mm. The flow path 3 extends through the predetermined ports 41 of a valve 4 and then connects with a manifold 6 in a port 10, followed by being divided into ten branched flow paths 7 in total via the manifold 6.

By the way, the number of the branched flow paths 7 is not limited to ten, and it may be suitably selected on the basis of the purpose of analysis. For the manifold 6, Z10M1 manufactured by VICI Co., Ltd. Or the like may be employed.

In the present embodiment, each of the branched flow paths 7 functions as a gradient-generating flow path and is formed with a stainless steel tube of 0.25 mm in inside diameter, 150 mm in length, and 7.5 µl in volume. In addition, they can function as eluent-storing means for temporarily storing the predetermined amounts of the respective eluents E having different compositions with different organic solvent ratios, pH values, salt concentrations, and so on, respectively. Furthermore, the lengths, volumes, and so on of the respective branched flow paths 7 can be suitably selected on the basis of the object.

Here, the liquid chromatograph of the present invention may be designed such that each of the branched flow paths 7 can be filled up with the eluent E directly fed from the syringe 5 by opening and closing the ports 41 of the valve 4. This cancels the time and effort for adjusting the piping each time to replace or supply the eluent.

The reference numeral 8 denotes a rotary valve provided with ten ports 81 connected with the ends of the respective branched flow paths 7. The valve 8 functions as a means for selecting eluents having different compositions and temporarily stored in the respective branched flow paths 7. In other words, the valve 8 is constructed such that the predetermined ports 81 are manually opened one after another to successively flow the eluents $E_1$, $E_2$, $E_3$, and so on with the desired compositions toward the devices downstream. Furthermore, a controller not shown in the figure is connected to the exit portion of the valve 8 to control the opening and closing of the valve on the basis of electric signals.

Furthermore, the branched flow paths may be filled up with eluents with different compositions under automatic controls.

Particularly, the eluents $E_1$, $E_2$, $E_3$, and so on having the predetermined compositions are automatically formulated and prepared for the respective branched flow paths 8, and then they are sequentially fed and stored in the respective branched flow paths 7.

The adoption of such a means allows an increase in purity of the eluent, so that it becomes possible to increase the precision of the analysis.

The eluent E selected by the operation of the valve 8 is directed to a sample-pouring part 9 by passing through the predetermined ports 41' of the valve 4 again. In this sample-pouring part 9, a previously prepared sample is poured into the eluent E by an injector (a sample-pouring device) 10.

As a method of pouring the sample Sm, there can be selected either of one by which the sample Sm is poured from the injector 10 into the flow path 3' or one by which the sample Sm is condensed in a trap column 11 and is then fed into the eluent E. Then, the sample Sm is transferred to a separation column 13 by the eluent E.

As an injector 10 can be suitably selected from those that satisfy the conditions of having pressure resistance, chemical resistance, and adhesiveness to prevent the sample Sm from the incorporation of air bubbles. In FIG. 1, the reference numeral 12 denotes a bath for a sample-remaining liquid.

Furthermore, a mixing device not shown in the figure may be mounted on the sample-pouring part 9 to perform a mixing between the eluent E and the sample S. As they are introduced in the mixing device, a gradient can be smoothly caused to make the width of a peak almost at constant. In addition, the eluents $E_1$, $E_2$, and so on having different compositions can be dispersed, so that a more linear base line can be formed.

Figure 2:
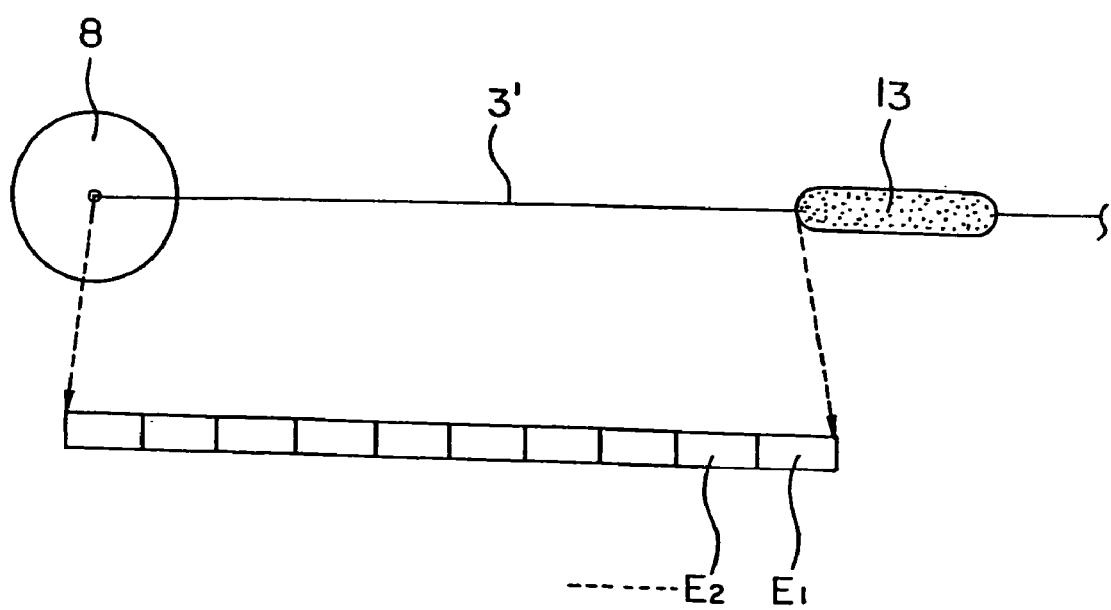
FIG. 2 is a schematic diagram showing the situation in which eluents $E_1$, $E_2$, and so on are stored in the flow path 3'.

Here, as shown in FIG. 2, at the time of starting the analysis, it is possible to previously feed and store the eluents $E_1$, $E_2$, and so on having different compositions from discharge orifices 82 of the valve 8 in the flow path 3' extending to a separation column mentioned later in order of a concentration gradient. Such a design allows the gradient elution to be performed within a short time from the initiation of the analysis, so that the time for analysis can be shortened.

Here, the reference numeral 13 denotes a separation column filled with a predetermined stationary phase (an octadecylsilane chemically bonded silica gel). In the present invention, as a separation column 13, one having an inside diameter of 0.5 mm or less is adopted so as to correspond to the flow of the eluent E at a low flow rate.

In the separation column 13, a solute component so contained in the sample Sm pored in the eluent E' is separated on the basis of the difference of affinity to the stationary phase, while eluting on the basis of variations of elution strengths of the respective eluents E1, E2, and so on having different compositions.

That is, the same procedures as those of such separation and elution, the eluents E1, E2, and so on having different compositions and stored in their respective branched flow paths 7 are sequentially selected and flowed to perform a high precision gradient elution of the sample component So.

The gradient-eluted solute component So can be subjected to an analysis such as a quantitative or qualitative determination by suitably selecting and using a detector 14 such as an absorption luminous-intensity (UV/VIS) detector, a fluorescence (FL) detector, a differential reflective index detector, an electrochemical detector, a chemiluminescence detector, and a mass spectrometer.

For instance, when the mass spectrometer is used as the detector 14, there can be provided a LC/MS capable of detecting the sample component with high sensitivity on the basis of a liquid chromatography capable of a high precision gradient elution. As an interface between the liquid chromatograph and the mass spectrometer, either of an electro spray (ESI) method or an atmospheric chemical ionization (APCI) method may be adopted.

Furthermore, in FIG. 1, the reference numeral 15 denotes a recorder connected to the detector 14 and the reference numeral 16 denotes a data processing device connected to the detector 14. The reference numeral 17 denotes a fraction collector connected to the detector 14 when the solution component So is fractionated, and the reference numeral 18 denotes a waste fluid tank.

EXAMPLE 1

A methanol solution of acetone was used as an eluent and the gradient change when the concentration of acetone in the methanol was changed by 10% was investigated using a UV detector at each of flow rates of 500 nL/min, 300 nL/min, and 100 nL/min.

In this experiment, the trap column 11, the separation column 13, and a mixing device were not used.

Figure 3:
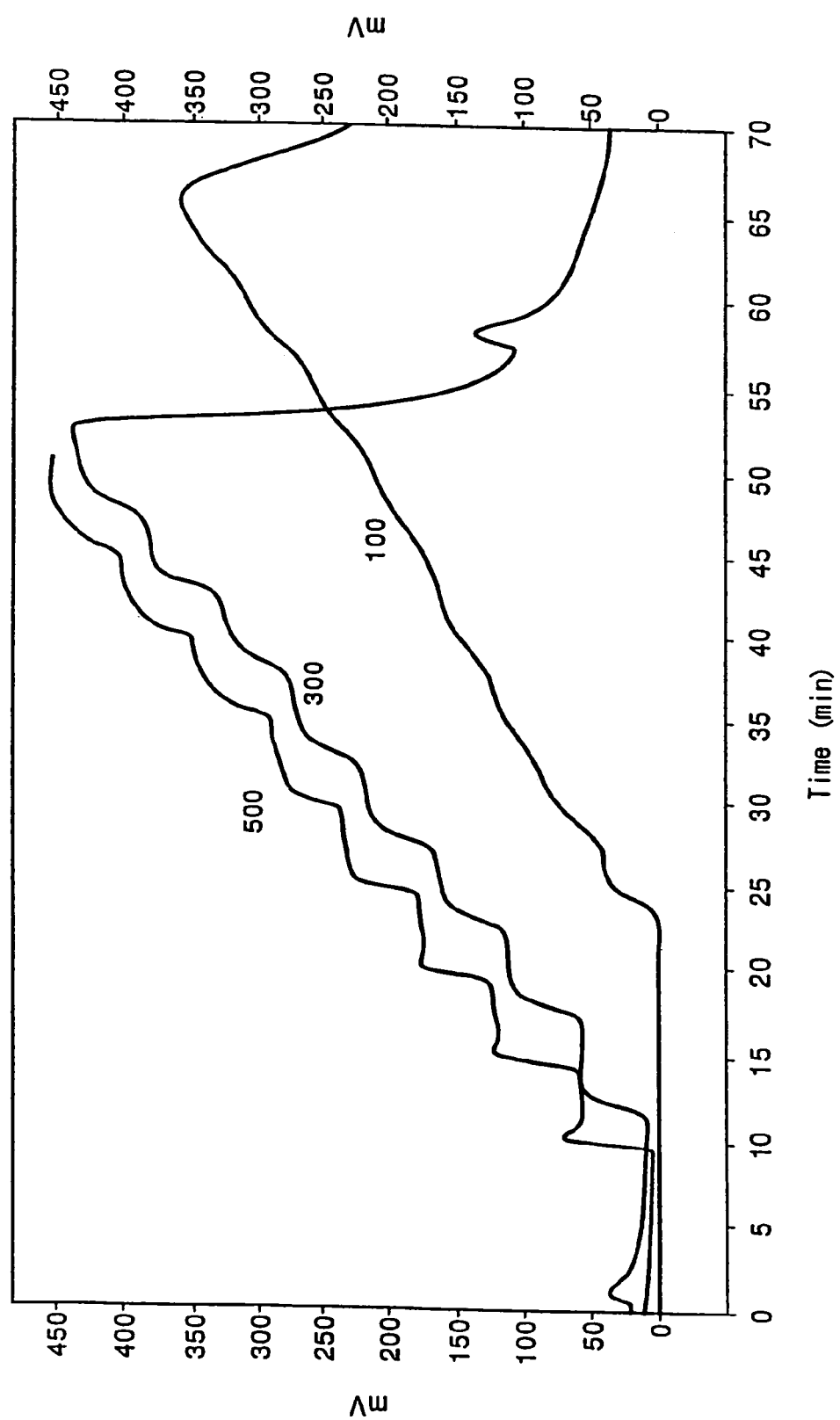
FIG. 3 is a diagram (graph) that shows a base line (a base line) drawn by the recorder 15 in Example 1.

FIG. 3 is a diagram (graph) that shows a base line drawn by the recorder 15 in Example 1. As shown in this gradient line, a stable gradient change is shown at each of the flow rates of 500 nL/min, 300 nL/min, and 100 nL/min. In particular, even at a low flow rate of 100 nL/min, a linear base line can be formed and thus it is enough to attain a linear gradient change of the eluent.

EXAMPLE 2

Using a mixing device, a methanol solution of acetone was used as an eluent and the gradient change when the concentration of acetone in the methanol was changed was investigated using a UV detector at each of flow rates of 300 nL/min and 100 nL/min.

Figure 4:
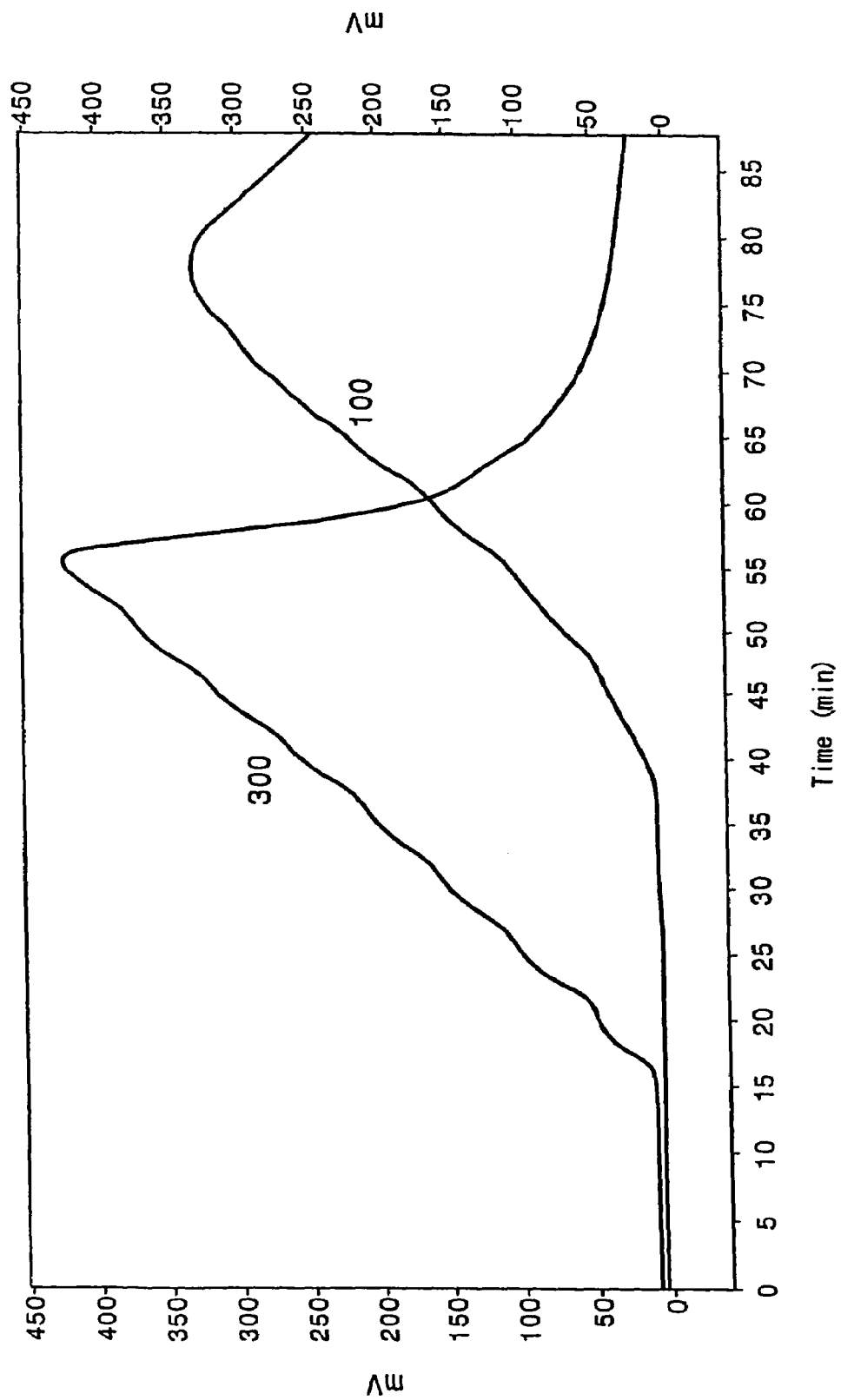
FIG. 4 is a diagram (graph) that shows a base line drawn by the recorder 15 in Example 2.

FIG. 4 is a diagram (graph) that shows a base line drawn by the recorder 15 in Example 3. As shown in this gradient line, a stable gradient change is shown at each of the flow rates of 300 nL/min and 100 nL/min. In particular, even at a low flow rate of 100 nL/min, a linear base line can be formed and thus it is enough to attain a linear gradient change of the eluent.

EXAMPLE 3

An experiment was carried out in order to prove that the analysis system of the present invention permits a high sensitive analysis of a peptide.

The sample used was a product of digesting calmodulin with the enzyme trypsin (a calmodulin trypsic digest) and the amount thereof was 150 fmoles.

The eluent used was one that comprises water, acetonitrile, and formic acid. The injection amount of the sample was 60 nL. The sample was directly introduced into a separation column. The flow rate was 300 nL/min. Furthermore, the range of molecular weight measured by a mass spectrometer was in the range of 600 to 1,500 Daltons.

Figure 5:
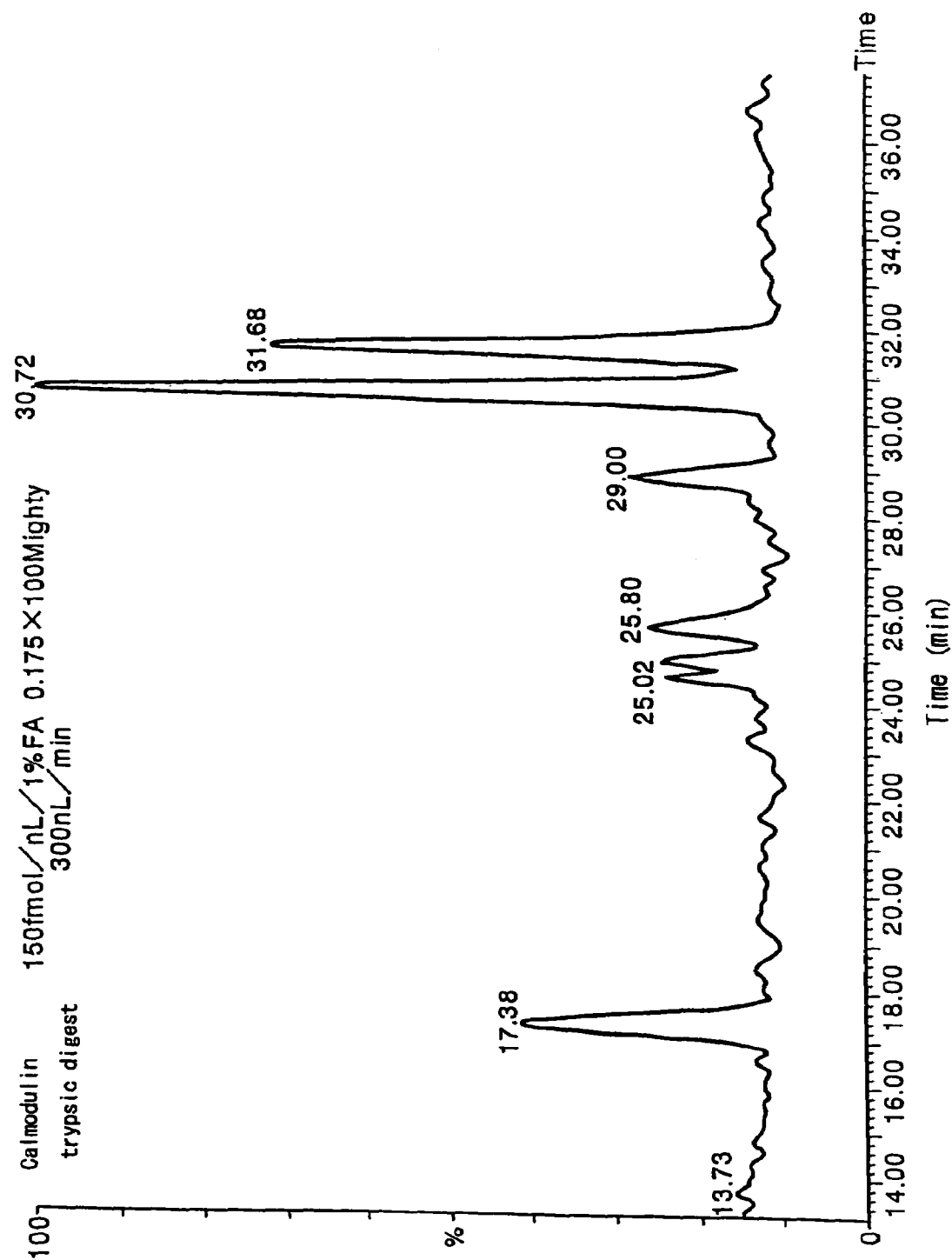
FIG. 5 is a diagram (a graph) showing a chromatograph of each mass component contained in the calmodulin trypsic digest.

FIG. 5 is a diagram (a graph) that shows a chromatograph of each mass component contained in the calmouldin trypsic digest. As various kinds of mass components form the respective sharp peaks, so that the separation of each sample component can be clearly found.

Figure 6:
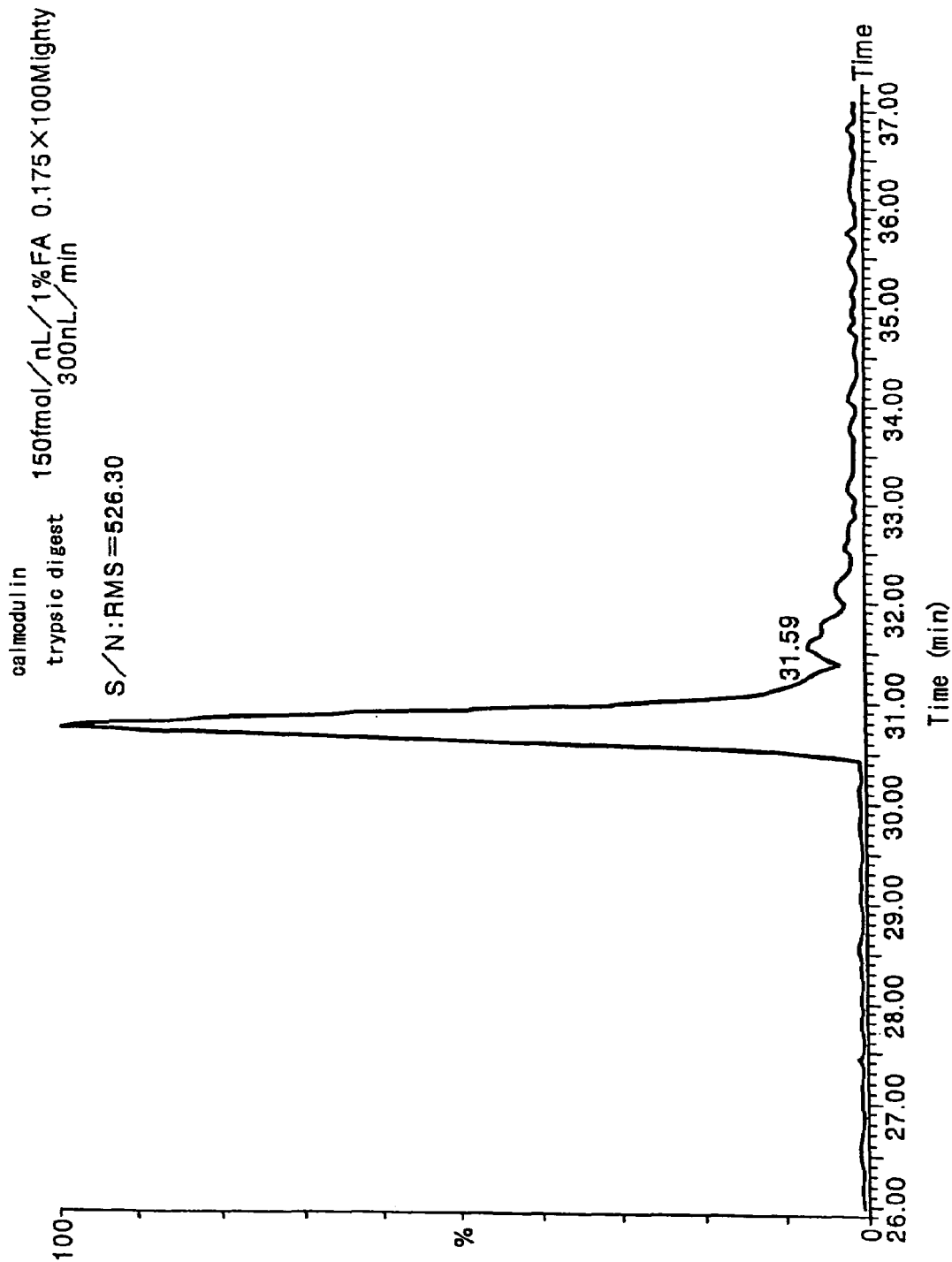
FIG. 6 is a diagram (a chromatograph) showing the results in which a peptide with 600 attomol (S/N=2) could be detected when the separated component with a highest total mass was detected by a single ion monitor.

FIG. 6 is a diagram (a chromatograph) showing the results in which a peptide with 600 attomol (S/N=2) could be detected when the separated component with a highest total mass was detected by a single ion monitor.

As described above, it is found that the analysis system (LC/MS) of the present invention the components of a sample are separated with high precision and the separated components are detected with high sensitivity.

INDUSTRIAL APPLICABILITY (1) The liquid chromatograph of the present invention allows an eluent with a flow rate of 500 nL/min or less to flow sequentially at a constant flow rate with reliability. Therefore, it becomes possible to carry out a gradient elution of solute components contained in the sample with high precision.

(2) The gradient elution method of the present invention is designed to temporarily store predetermined amounts of eluents having different compositions at a position in a flow path upstream from a sample-pouring means. Therefore, an eluent having a desired composition can be easily fed in a stepwise or continuous manner with desired timing as needed.

(3) It is constructed such that only one high-pressure liquid-feeding pump is used and eluents can be fed into the respective branched flow paths by a switching movement of a valve. Therefore, comparing with the configuration of an apparatus in which a plurality of high-pressure liquid-feeding pump is used for feeding to the respective branched flow paths, the apparatus can be made compact, the flow rate of an eluent can be controlled more simply, and a correct gradient can be attained because no backflow of a solvent depending on the compression rate occurs.

(4) The synthesis system of the present invention comprises a liquid chromatograph which is constructed to carry out the gradient elution of a solute with high precision, so that the separation of solute components can be performed with high precision and the separated components can be detected with high sensitivity.

The invention claimed is:

1. A liquid chromatograph for introducing a sample into a separation column with eluents having different compositions successively fed through a flow path and performing a gradient elution of a solute in the sample depending on elution strengths of the eluents, comprising:
   one high-pressure liquid-feeding pump for feeding the eluent at a constant rate;
   an eluent-storing means for temporarily storing the eluents having different compositions in branched flow paths having predetermined volumes, where the branched flow paths are formed by dividing the flow path of the eluents fed from the high-pressure liquid-feeding pump; and
   an eluent-selecting means for successively selecting the eluents temporarily stored in the branched flow paths and feeding the eluents toward the separation column.

2. The liquid chromatograph as set forth in claim 1, further comprising:
   a means for filling the branched flow paths respectively with the eluents from a syringe by a switching movement of a valve.

3. An analysis system, comprising a mass spectrometer connected to the liquid chromatograph set forth in claim 1 or claim 2.

4. A gradient elution method, comprising the use of the liquid chomatograph set forth in claim 1.

5. The gradient elution method as set forth in claim 4, wherein the eluents having different compositions are successively fed from the respective branched flow paths to a flow path extending from a discharge orifice of the respective branched flow paths to the separation column and stored therein in advance.

6. A liquid chromatograph, which is constructed to introduce a sample into a separation column with eluents having different compositions sequentially fed through a flow path and perform a gradient elution of a solute in the sample depending on elution strengths of the eluents, comprising:
   an eluent-storing means for temporarily storing the eluents having different compositions in branched flow paths having predetermined volumes, where the branched flow paths are formed by dividing the flow path of the eluents; and
   an eluent-selecting means for sequentially selecting the eluents temporarily stored in the branched flow paths and feeding the eluents toward the separation column.

7. The liquid chromatograph as set forth in claim 6, further comprising:
   a means for filling the branched flow paths respectively with the eluents from an injector by a switching movement of a valve.

8. An analysis system, comprising a mass spectrometer connected to the liquid chromatograph as set forth in claim 6 or claim 7.

9. A gradient elution method, comprising the use of the liquid chromatograph set forth in claim 6 or claim 7.

* * * * *